United States Patent
Valdevit et al.

(10) Patent No.: US 8,110,004 B2
(45) Date of Patent: Feb. 7, 2012

(54) EXPANDABLE INTERBODY FUSION CAGE WITH ROTATIONAL INSERT

(75) Inventors: Antonio Valdevit, Effort, PA (US);
Vikki Hazelwood, Wayne, NJ (US);
Steven J. Gadol, Bridgewater, NJ (US);
Frederick H. Hardenbrook, Egg Harbor Township, NJ (US); William J. Kowalski, Pompton Lakes, NJ (US);
Adrienne G. Quiray, Jersey City, NJ (US); Michael A. Trapani, Staten Island, NY (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 403 days.

(21) Appl. No.: 12/545,173

(22) Filed: Aug. 21, 2009

(65) Prior Publication Data
US 2010/0049324 A1 Feb. 25, 2010

Related U.S. Application Data

(60) Provisional application No. 61/090,769, filed on Aug. 21, 2008.

(51) Int. Cl.
*A61F 2/44* (2006.01)
(52) U.S. Cl. .................................................. 623/17.16
(58) Field of Classification Search ..... 623/17.11–17.16
See application file for complete search history.

(56) References Cited

U.S. PATENT DOCUMENTS

| | | | |
|---|---|---|---|
| 4,863,476 A | 9/1989 | Shepperd | |
| 5,059,193 A | 10/1991 | Kuslich | |
| 5,653,763 A | 8/1997 | Errico et al. | |
| 5,658,336 A | 8/1997 | Pisharodi | |
| 5,665,122 A | 9/1997 | Kambin | |
| 5,693,100 A | 12/1997 | Pisharodi | |
| 6,117,174 A | 9/2000 | Nolan | |
| 6,126,689 A | 10/2000 | Brett | |
| 6,129,763 A | 10/2000 | Chauvin et al. | |
| 6,159,244 A | 12/2000 | Suddaby | |
| 6,174,334 B1 | 1/2001 | Suddaby | |
| 6,176,882 B1 * | 1/2001 | Biedermann et al. | 623/17.15 |
| 6,183,517 B1 | 2/2001 | Suddaby | |
| 6,332,895 B1 | 12/2001 | Suddaby | |
| 6,375,683 B1 * | 4/2002 | Crozet et al. | 623/17.15 |
| 6,419,705 B1 | 7/2002 | Erickson | |
| 6,436,140 B1 | 8/2002 | Liu et al. | |
| 6,443,989 B1 | 9/2002 | Jackson | |
| 6,454,807 B1 | 9/2002 | Jackson | |
| 6,520,991 B2 | 2/2003 | Huene | |
| 6,613,089 B1 | 9/2003 | Estes et al. | |

(Continued)

*Primary Examiner* — Eduardo C Robert
*Assistant Examiner* — Stuart S Bray
(74) *Attorney, Agent, or Firm* — Greenberg Traurig, LLP

(57) ABSTRACT

An expandable intervertebral fusion cage that includes an inferior baseplate and a superior baseplate, an insert rotatably received between the inferior and superior baseplates, and a guide pin coupled to the inferior and superior baseplates for facilitating the rotation of the insert. The insert includes a pair of protuberances, each of which are releasably engageable with a corresponding lock groove formed within the inferior and superior baseplates. When said insert is rotated relative to the guide pin, the protuberances engage the lock grooves, and the inferior and superior baseplates expand from a collapsed position, in which said inferior and superior baseplates are juxtaposed with one another, and an expanded position, in which said inferior and superior baseplates are diverged away from one another. Tabs formed on the superior baseplate continuously engage slots formed within the inferior baseplate when the baseplates expand from their collapsed position to their expanded position.

9 Claims, 3 Drawing Sheets

U.S. PATENT DOCUMENTS

| | | |
|---|---|---|
| 6,652,584 B2 | 11/2003 | Michelson |
| 6,723,128 B2 | 4/2004 | Uk |
| 6,793,679 B2 | 9/2004 | Michelson |
| 6,808,537 B2 | 10/2004 | Michelson |
| 6,814,756 B1 | 11/2004 | Michelson |
| 6,830,589 B2 | 12/2004 | Erickson |
| 6,962,606 B2 | 11/2005 | Michelson |
| 6,972,035 B2 | 12/2005 | Michelson |
| 7,008,453 B1 | 3/2006 | Michelson |
| 7,018,415 B1 | 3/2006 | McKay |
| 7,118,598 B2 | 10/2006 | Michelson |
| 7,217,293 B2 | 5/2007 | Branch, Jr. |
| 7,297,162 B2 | 11/2007 | Mujwid |
| 7,488,330 B2 * | 2/2009 | Stad .............. 606/102 |
| 7,641,693 B2 * | 1/2010 | Gutlin et al. .............. 623/17.15 |
| 7,708,778 B2 * | 5/2010 | Gordon et al. ............. 623/17.15 |
| 7,708,779 B2 * | 5/2010 | Edie et al. ................. 623/17.15 |
| 2005/0060036 A1 * | 3/2005 | Schultz et al. ............. 623/17.15 |
| 2005/0278036 A1 * | 12/2005 | Leonard et al. ............ 623/23.47 |
| 2006/0129244 A1 | 6/2006 | Ensign |
| 2006/0241767 A1 * | 10/2006 | Doty ........................... 623/17.12 |
| 2009/0265007 A1 * | 10/2009 | Colleran .................... 623/17.16 |

* cited by examiner

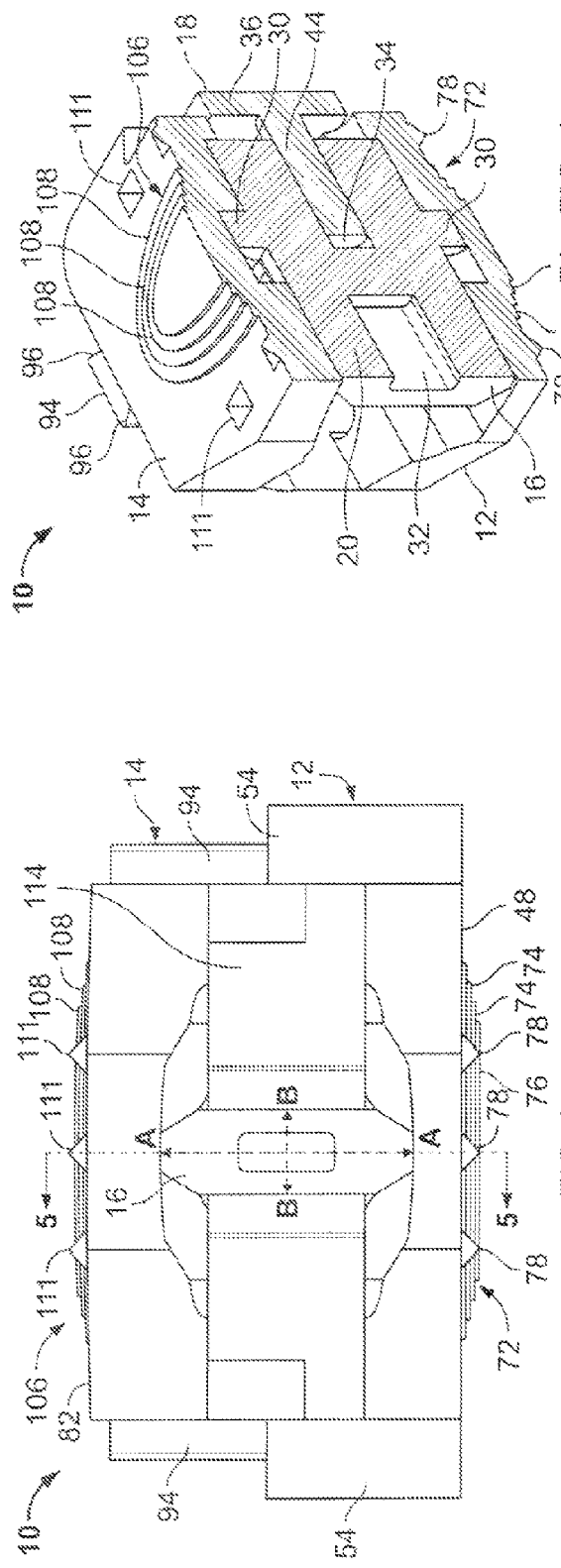
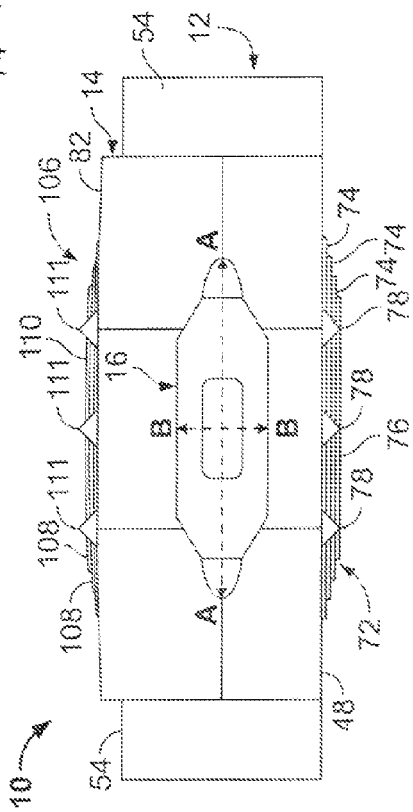

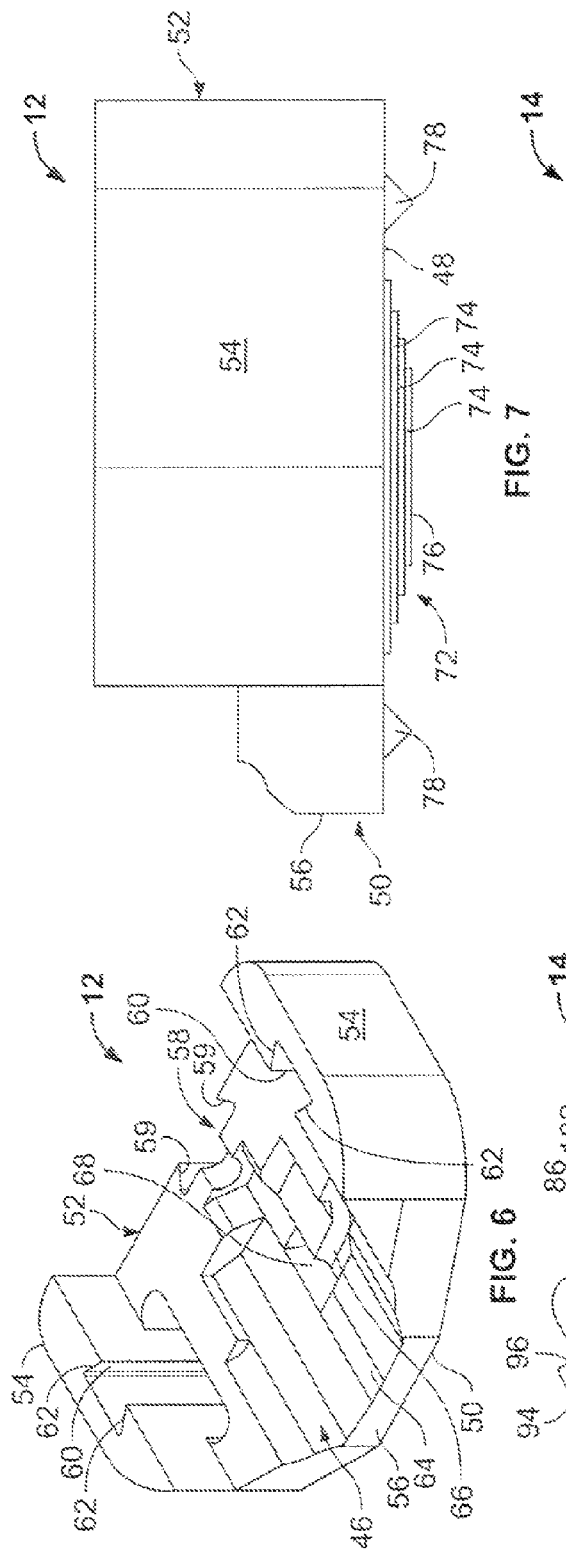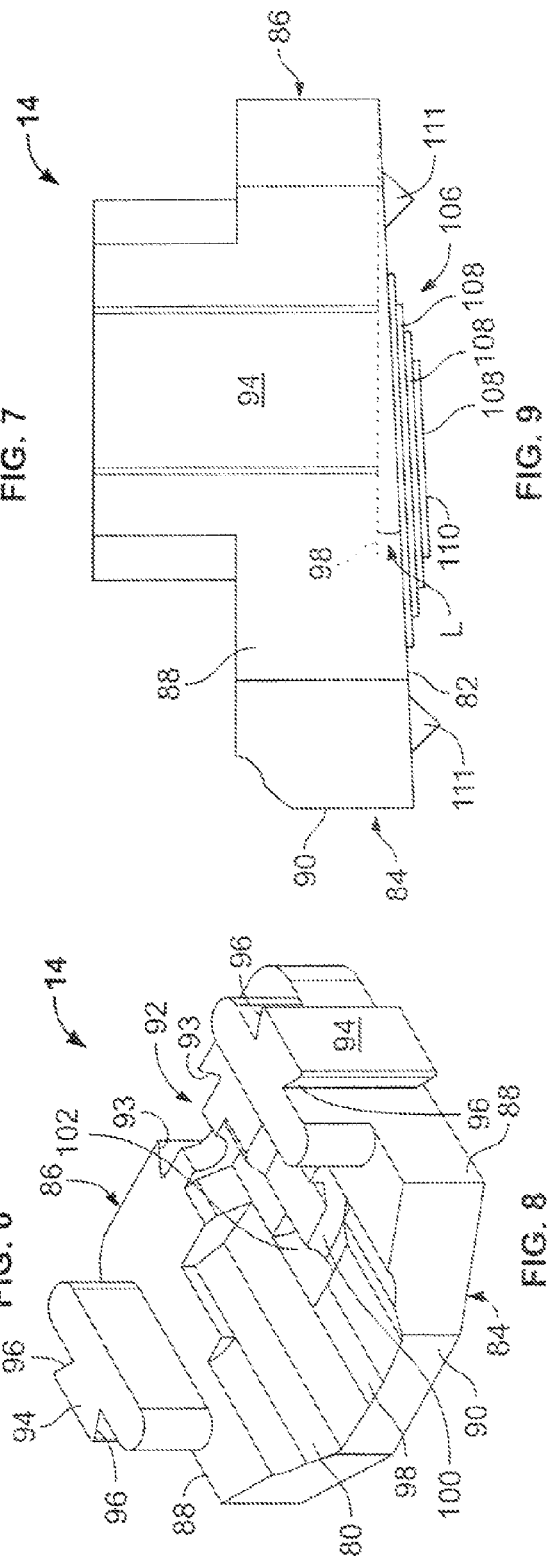

EXPANDABLE INTERBODY FUSION CAGE WITH ROTATIONAL INSERT

CROSS-REFERENCE TO RELATED APPLICATION

This application is a Section 111(a) application relating to commonly owned, U.S. Provisional Application Ser. No. 61/090,769 entitled "EXPANDABLE INTERBODY FUSION CAGE WITH ROTATIONAL INSERT" filed Aug. 21, 2008.

FIELD OF THE INVENTION

The present invention relates to medical devices used in orthopaedic spinal fusion procedures and, more particularly, expandable interbody fusion cages used in spinal fusion procedures.

BACKGROUND OF THE INVENTION

Annually, there are approximately 300,000 fusion surgeries performed in the United States. Numerous types of spinal fusion cages exist, varying in design, material, size, and implantation method. Regardless of the type of cage used, a full or partial discectomy is performed prior to implantation. Once the necessary portion of a spinal disc is removed, the disc space is then expanded using a distracter. In order to accept a cage, the disc space must be distracted so that the intervertebral height can be reestablished. Distraction also enhances stability by tensioning the ligamentous apparatus, which increases the compressive forces that hold the cage in place. The amount of disc space distraction is a crucial aspect of the spinal fusion surgery; too little or too much distraction results in various complications that compromise the clinical outcome of the surgery.

All of the current fusion cages can be classified as either threaded or non-threaded fusion cages. Threaded fusion cages are typically cylindrical in shape and are implanted by screwing the cage between the adjacent vertebrae to reestablish the disc space height. Before implantation, the surgeon prepares the vertebral endplates with a reamer, creating a channel for the cage, and then threads the channel using a threading device. By creating the channel parasagitally across the disc space, the vascular cancellous bone is exposed, creating an optimal bleeding bed to promote fusion. However, the strong subchondral bone of the cortical endplate is partially removed, which compromises the endplate's integrity.

Non-threaded cages are typically either box (e.g., rectangular) in shape or cylindrical in shape, and are implanted by impacting the cage into the disc space, reestablishing the intervertebral height. Before implantation, the endplate cartilage is removed in order to expose the bleeding bone. The cage is then inserted into the disc space, usually anchored by saw teeth or spikes, securing it between the adjacent vertebrae. Since only the endplate cartilage is removed, the subchondral bone is preserved, leaving the strongest bone adjacent to the cage. The disc space can also be filled with a greater quantity of bone graft (if used) when compared to the threaded cage, as the cage itself takes up less of the disc space volume. This increased bone graft volume increases the fusion rate. However, the endplate is minimally vascularized, which may delay or impede fusion. The cage must also be precisely the correct height to match the disc space in order for implantation to occur; a factor that makes the implantation of these cages significantly difficult.

When performing an interbody fusion, an anterior or posterior approach is generally used. There is no overall preference as to which surgical approach is to be used, since it is based on the spinal anatomy and the patient's prior surgical history. Anterior lumbar interbody fusion (ALIF) involves accessing the spine through the abdomen. A posterior lumbar interbody fusion (PLIF) procedure gains access to the disc space through the back, avoiding potential complications related to major vascular structures and sympathetic injury. Both the threaded and non-threaded cage varieties can be implanted using either approach.

When implanting a fixed cage, an extensive preparation of vertebral endplates is required in order to properly fit the cage into the disc space. This extensive site preparation can damage the endplates, compromising the integrity of the vertebrae. Since the cage is a fixed height, the surgeon must predetermine the size of the implant. If the cage is too large or too small, the surgeon is forced to coerce the implant to fit into the disc space, risking a malpositioned cage and revision surgery.

An interbody fusion procedure is associated with a 5-10% risk of complication. The vast majority of these complications arise from the surgical procedure used to implant the cage; there are few reported cases of the cage itself failing mechanically. The more common, minor complications resulting from the fusion procedure include dural tears, ileus, superficial infections, and neurologic problems. Other, more serious complications include subsidence, nonunion, device migration, and malpositioning. These complications usually result in a revision surgery, in which the surgeon must perform a second procedure to remove the initial cage, repair any damage, and implant a new device.

Subsidence occurs when the implant penetrates the vertebral endplate. This penetration itself can cause pain and lead to a loss of the disc space height that was originally achieved. The loss of disk space height negates the implant and the spine is once again unstable. This instability leads to revisions in an attempt to alleviate the pain and re-space the vertebrae again. Subsidence also causes a narrowing of intervertebral foramen and loss of lordsosis, which further exacerbates patient discomfort and can impair the patient's balance. The problem of subsidence is one of the most prominent in spinal fusions. However, it has been found that having a footprint surface area of the implant greater than 40% the surface area of the vertebral endplate greatly reduces the incidence of subsidence.

Nonunion, or pseudarthrosis, is a major concern in interbody fusion as it negates the desired effect. Pseudarthrosis can occur for several reasons, the most common involving motion about the cage. An improperly sized implant may fail to gain adequate purchase into the bony endplates, leading to laxity and nonunion. In order for a proper fusion to take place, the surrounding bone must be subjected to sufficient loads so that bone formation is generated. Further, micromotions of the implant and implant-bone interface must be kept to a minimum to promote bone ingrowth. At micromotions above 24 μm, fibrous tissue ingrowth begins to occur, which impedes bone ingrowth and creates an improper fusion. If pseudarthrosis occurs, a revision surgery is performed so that the segment can be properly stabilized.

In extreme cases of nonunion, device migration can occur. A cage that is not securely fixed to the adjacent vertebrae can migrate anteriorly or posteriorly, both of which have drastic effects. Anterior migration results in the cage moving into the abdomen. During motion, the migrating implant can tear major vascular structures and organs, causing extensive complications and even death. If the cage migrates posteriorly, it can shift into the medullary canal, damaging the spinal cord, causing paralysis and death. An implant migration requires immediate revision surgery. These revisions are especially taxing, as the implant must be located and extracted and any extensive damage it may have caused must be repaired.

A malpositioned cage can be the underlying cause for a variety of complications, including the three previously discussed. A cage that is malpositioned is one that either does not appropriately fit the disc space or was implanted in an incorrect manner. Malpositioning can be the result of a poorly designed cage, an inappropriate device selection, or surgeon error. The faulty placement of the cage can result in decreased stability, which can cause pseudarthrosis or migration. A cage that is inappropriately sized can increase the risk of subsidence or compress surrounding nerve roots. Since the positioning of the cage is causing substantial complications, a malpositioned cage must be removed and replaced via a revision surgery.

These four complications account for the vast majority of revision surgeries performed. Each year in the United States, approximately 6% of fusions result in revision surgery. Other complications, such as vascular and neurological injury are more frequent, but normally do not require a revision surgery. The main vascular injuries that were found included arterial thrombosis, venous thrombosis, and lacerations. The complications resulting in a revision surgery are mostly due to the surgical procedure involved in interbody fusion.

The endplate preparation required to implant the cage also causes endplate abrasion and is further exacerbated during the implantation of the cage, in which the surgeon must coerce the implant into the disc space. This situation is particularly common with non-threaded cages. The surgeon distracts the disc space to the same height as the cage, therefore requiring substantial force to impact the cage into the void. The shear stresses against the vertebrae erode the endplates, damaging their surfaces. This trauma to the endplates initiates an inflammatory response, which can delay or inhibit fusion. The lack of stability of the implant can then result in pseudarthrosis or migration, requiring a revision surgery.

During a fusion surgery, the intricate procedure required to implant the cage often leads to surgeon error. A more common surgeon error is an inaccurate distraction of the intervertebral space. The amount of distraction is one of the most important aspects of a fusion surgery. Over-expansion can stretch and irritate the surrounding muscular and neural tissue, while too little expansion will not allow for adequate tensioning of the ligamentous apparatus, decreasing the stability of the cage. Subsidence, pseudarthorsis, or possibly migration could result, necessitating a revision surgery.

X-rays are generally used to assess the disc space height in order to select a cage of the appropriate size. Height will be measured again during surgery, but once the cage is implanted, the height cannot be adjusted. The height of the implant is one of the most important aspects of the fusion surgery. Over-distraction from implants that are too tall will stretch the surrounding neural and muscular tissue, causing irritation. The widened disc space will also compress the adjacent discs, placing them under abnormal stresses and depleting their shock absorbing function. The large implant will be more likely to subside into the surrounding vertebrae, as the disc space will attempt to return to its normal height. An implant that is too small will fail to gain sufficient purchase into the vertebral endplates, resulting in pseudarthrosis and possibly migration. In both cases, the risk of malpositioning is increased, since the implant is inherently poorly suited for the intended space. A revision surgery will most likely be required.

The revision surgery is strenuous for both the surgeon and patient. Revision surgeries are generally longer and more extensive than the original surgery, as the faulty implant must first be removed. This increased surgical time imposes more trauma to the patient, and is usually associated with a significantly increased recovery time. The revision surgery also increases health care costs, requiring the hospital to spend substantial funds.

A significant portion of complications that lead to a revision surgery are caused by a mismatch between the intervertebral height and fusion cage, which is mostly due to the fixed height nature of the current cages. Since the surgeon must determine the height of the cage before implantation, any error in this measurement will result in a mismatch between cage and disc space height. The surgeon is unable to alter the height intraoperatively, and must therefore coerce the cage to fit or, if available, implant a different cage. Even if the cage is sized appropriately, some coercion is needed to impact the cage into the disc space, resulting in endplate abrasion and possible malposition.

To summarize, current fixed cages present the potential problems of abrasion, subsidence, malpositioning, pseudoarthritis, and even cage migration, all of which create potential further future expense and pain for patients and clinicians by means of the need for revision surgeries. What is needed, therefore, is a cage that minimize or eliminate the foregoing problems characterized by fixed cages.

SUMMARY OF THE INVENTION

The present invention overcomes the disadvantages and shortcomings of the prior art discussed above by providing an expandable interbody fusion cage that includes an inferior baseplate, a superior baseplate, an insert mounted rotatably between the inferior and superior baseplates, and a guide peg that facilitates the rotation of the insert. Expansion of the cage is achieved by rotating the insert 90° within the inferior and superior baseplates from its initial collapsed position to its final expanded position. Each of the inferior and superior baseplates includes an external surface adapted for interaction with a vertebral body, and an internal portion adapted to house and guide the insert during rotation. The external surfaces of the inferior and superior baseplates incorporate geometry to match the natural shape and curvature of the vertebral endplate and gain purchase into the endplate to secure the cage in place. The external surface of the superior baseplate is also angled to account for the lordosis of the spine. The internal surfaces of the baseplates incorporate various grooves and curves so as to enclose the insert and prevent unwanted motion during its rotation. The baseplates are designed to interact with each other, being in constant contact once assembled to further guide the expansion and prevent unwanted motion.

The guide peg includes a solid axle from which the insert rotates about, interacting with the insert as well as the inferior and superior baseplates. The guide peg fits into a slot formed within the inferior and superior baseplates when the cage is assembled. When the insert is placed into the assembly, it engages the guide peg, ensuring that the insert is centered within the baseplates and stabilized during rotation.

The insert drives the expansion of the cage. In an embodiment, the insert is oval in shape and includes dog-eared, angled, flat edges. Such a size and shape allows for the insert's rotation to cause expansion of the cage, as the insert's major axis is longer than its minor axis. The insert is initially placed into the cage with its minor axis vertical, and is then rotated 90° so that its major axis becomes vertical. This rotation forces the two baseplates apart, thus expanding the cage. The insert is guided during the rotation by the guide peg and grooves within the internal surfaces of the inferior and superior baseplates. The insert is secured into its final conformation by pushing it posteriorly into another groove within the interior surfaces of the baseplates. In its locked position, the insert is prevented from dis-rotating and, thus avoids a collapse of the cage.

In an embodiment, each of the four main components described above are interchangeable, as they may consist of different sizes, shapes, etc., so as to allow for enhanced adjustability of the cage. The superior baseplate is selected to match the lordosis angle of the operated segment, and an insert is selected to achieve the desired final height once the cage is expanded. This adjustability enhances the fit and positioning of the cage.

Further features and advantages of the invention will appear more clearly on a reading of the detailed description of exemplary embodiments of the invention, which is given below by way of example only with reference to the accompanying drawings.

BRIEF DESCRIPTION OF THE DRAWINGS

For a better understanding of the present invention, reference is made to the following detailed description of an exemplary embodiment considered in conjunction with the accompanying drawings, in which:

FIG. 3 is a front elevational view of the cage shown in FIG. 1;

FIG. 4 is a top perspective cross-sectional view, taken along line 5-5 and looking in the direction of the arrows, of the cage shown in FIG. 3, FIG. 5 is a front elevational view of the cage shown in FIG. 1, but with the cage being shown in a non-expanded (i.e., collapsed) position;

FIG. 6 is a top perspective view of an inferior baseplate employed by the cage shown in FIGS. 1-5;

FIG. 7 is a side elevational view of the inferior baseplate shown in FIG. 6;

FIG. 8 is a bottom perspective view of a superior baseplate employed by the cage shown in FIGS. 1-5; and FIG. 9 is a side elevational view of the superior baseplate shown in FIG. 8.

DETAILED DESCRIPTION OF THE EXEMPLARY EMBODIMENT

Figure 1:
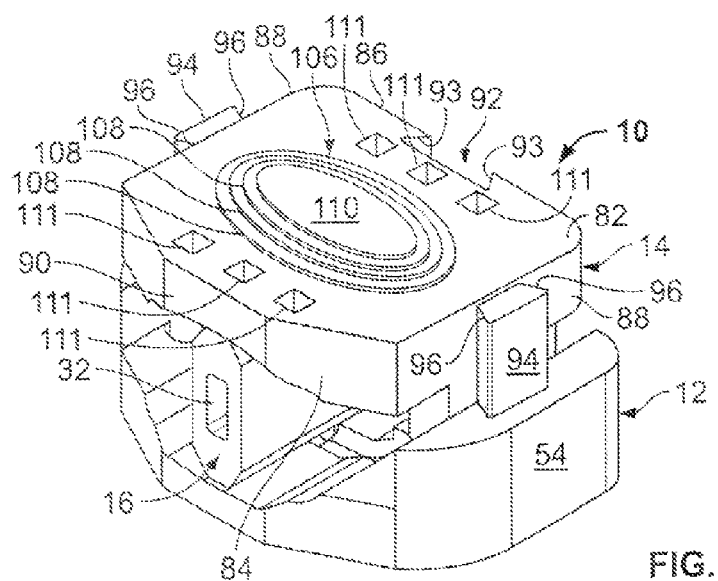
FIG. 1 is a top, perspective view of an expandable fusion cage constructed in accordance with an exemplary embodiment, the cage being shown in an expanded, position.
Figure 2:
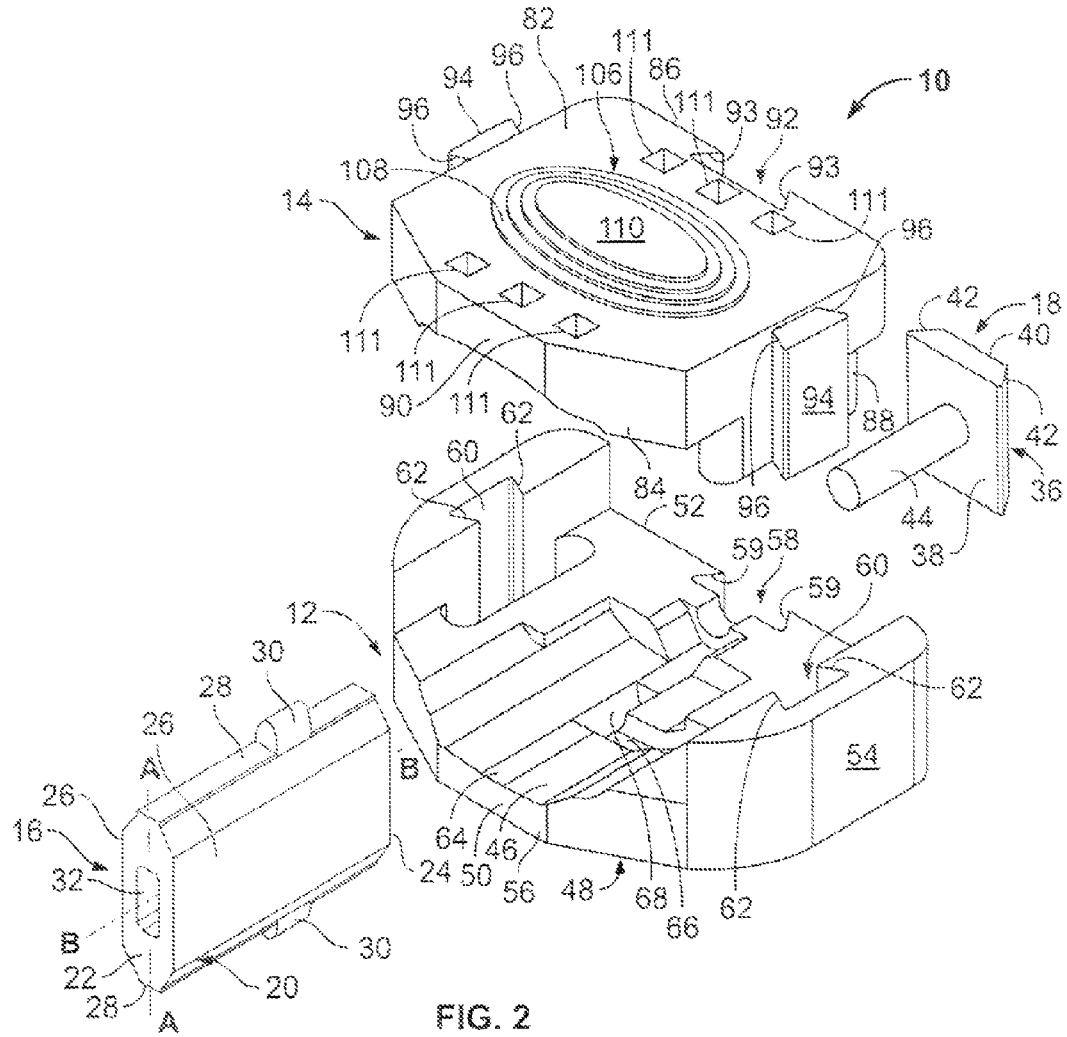
FIG. 2 is an exploded, top perspective view of the cage shown in FIG. 1.

Referring to FIGS. 1 through 5, a fusion cage 10 includes an inferior baseplate 12 and a superior baseplate 14 which is movably connected to the inferior baseplate 12, an insert 16, and a guide peg 18 (see FIGS. 2 and 4). The insert 16 is rotatably assembled to the guide peg 18, and is positioned between the inferior and superior baseplates 12, 14 for purposes that are described below. The cage 10 is adapted to expand from a contracted (i.e., collapsed) position, as shown in FIG. 5, to an expanded position, as shown in FIG. 1.

Referring to FIGS. 2 and 4, the insert 16 includes a body 20 that has proximal and distal ends 22, 24, side surfaces 26 that extend parallel to major axis A-A of the insert 16, and surfaces 28 that extend parallel to minor axis B-B of the insert 16. Protuberances 30 extend outwardly from the surfaces 28. A rectangular-shaped cavity 32 is formed within the proximal end 22 of the insert 16 to accept the insertion of a tip of a screw-driver like hand tool (not shown in the Figures). A circular shaped cavity 34 is formed within the distal end 24 of the insert 16 (see in particular FIG. 4) to accept the insertion of the guide peg 18. The distance between the surfaces 28 is nominally 6-13 millimeters, although other distances may be provided, depending on the needs of the cage 10. The distance between the side surfaces 26 is nominally five millimeters, although other distances may also be provided.

Continuing to refer to FIGS. 2 and 4, the guide peg 18 has a square-shaped base 36 which has proximal and distal surfaces 38, 40 and beveled edges 42. A round peg 44 projects outwardly from the proximal surface 38 of the base 36. The peg 44 provides an axle about which the insert 16 rotates. More particularly, the peg 44 of the guide peg 18 is positioned inside the cavity 34 of the insert 16 such that the insert 16 is free to rotate about the peg 44 in a manner which is described below.

Referring to FIGS. 2-7, the inferior baseplate 12 has inner and outer surfaces 46, 48 which are flanked by proximal and distal ends 50, 52, and side sections 54. The proximal end 50 has a flat area 56, and the distal end 52 has a slot 58 with beveled edges 59 to facilitate the movable interconnection of the peg guide 44 with the inferior baseplate 12. Interlocking slots 60 having beveled edges 62 are formed internally within each of the side sections 54 to facilitate the movable interconnection of the inferior baseplate 12 to the superior baseplate 14.

With particular reference to FIGS. 2 and 6, the inner surface 46 of the inferior baseplate 12 is sized and shaped to movably interconnect with the insert 16 and the peg guide 18. For this purpose, the inner surface 46 includes a bearing surface 64, a guide groove 66, a lock groove 68, and the guide peg slot 58.

The outer surface 48 of the inferior baseplate 12 is sized and shaped to interconnect with vertebral bodies (not shown in the Figures). With particular reference to FIGS. 3-5 and 7, the outer surface 48 has a convex shaped area or dome 72 which includes a staircase pattern of oval-shaped terraces 74 and a flat plateau 76 centrally located on the dome 72. The dome 72 is contoured to fit the concavity of the vertebral endplate (not shown in Figures). A plurality of pyramidal-shaped spikes 78 are disposed on the outer surface 48 of the inferior baseplate 12 for anchoring the cage 10 to the vertebral endplate.

Referring to FIGS. 2-5 and 8-9, the superior baseplate 14 has inner and outer surfaces 80, 82 which are flanked by proximal and distal ends 84, 86, and side sections 88. The proximal end 84 has a flat area 90, and the distal end 86 has a slot 92 with beveled edges 93 to facilitate the movable interconnection of the peg guide 18 with the superior baseplate 14. Interlocking tabs 94 having beveled edges 96 are formed externally on each of the side sections 88 to facilitate the movable interconnection of the superior baseplate 14 to the inferior baseplate 12. In this regard, each of the slots 60 of the inferior baseplate 12 is sized and shaped to receive slidably a corresponding one of the tabs 94 of the superior baseplate 14.

With particular reference to FIG. 8, the inner surface 80 of the superior baseplate 14 is sized and shaped to movably interconnect with the insert 16 and the peg guide 18. For this purpose, the inner surface 80 includes a bearing surface 98, a guide groove 100, a lock groove 102, and the guide peg slot 92.

The outer surface 82 of the superior baseplate 14 is sized and shaped to interconnect with vertebral bodies (not shown in the Figures). Still referring to FIGS. 2-5 and 8-9, the outer surface 82 has a dome 106 which includes a staircase pattern of oval-shaped terraces 108 and a flat plateau 110 centrally located on the dome 106. The plane of the plateau 110 is parallel with the plane of the outer surface 82. The dome 106 is contoured to mate with the concave surface of the vertebral endplate. A plurality of pyramidal-shaped spikes 111, which are identical in size and shape to the spikes 78 of the inferior baseplate 12, are disposed on the outer surface 82 of the superior baseplate 14 to facilitate anchoring the superior baseplate 14 to the vertebral endplate. With reference to FIG. 9, an angle L is provided between the bearing surface 98 and the outer surface 82 of the superior baseplate 14. The angle L is varied to match the lordotic angle of the spine and is nominally in the range of, but is not limited to 3 to 12 degrees. In another embodiment, the superior base plate need not be angled.

In an embodiment, the inferior and superior baseplates 12, 14 are generally D-shaped so as to match the general geometry of vertebral endplates and allow for better seating of the cage 10 into the vertebral bodies. In an embodiment, the inferior and superior baseplates 12, 14 are each sized and shaped so that no less than 40% of the surface area of each of the vertebral endplates comes into contact with the outer surfaces 48, 82 of the inferior and superior baseplates 12, 14, respectively. The spikes 78, 111 facilitate the engagement between the cage 10 and the vertebral endplates. Each set of the spikes 78, 111 are arranged in two parallel rows of three, although other suitable arrangements may be provided. In an embodiment, one row of the spikes 78, 111 is located adjacent to each of the proximal ends 50, 84 of the inferior and superior baseplates 12, 14, respectively, and another row of spikes 78, 111 is located adjacent to each of the distal ends 52, 86 of the inferior and superior baseplates 12, 14, respectively. The rows of spikes 78, 111 are centrally arranged between the corresponding side sections 54, 88 of the inferior and superior baseplates 12, 14, respectively. In an embodiment, the inferior and superior baseplates 12, 14, the insert 16, and the guide peg 18 are made of a rigid biocompatible material (e.g., titanium, stainless steel, polymer, etc.).

The interconnection of the superior baseplate 14 with the inferior baseplate 12 is facilitated by inserting the tabs 94 of the superior baseplate 14 within the corresponding slots 60 of the inferior baseplate 12. The contiguous positioning of the beveled edges 96 of the tabs 94 with the corresponding beveled edges 62 of the slots 60 prevents the superior baseplate 14 from tilting or rotating with respect to the inferior baseplate 12, and vice versa. The tabs 94 and beveled edges 96 of the superior baseplate 14 are sized and shaped to freely slide and remain in constant contact with the slots 60 and the beveled edges 62 of the inferior baseplate 12 during expansion of the cage 10.

The interconnection of the guide peg 18 with the inferior and superior baseplates 12, 14 is facilitated by the positioning the beveled edges 42 of the base 36 of the guide peg 18 within the corresponding slots 58, 92 of the inferior and superior baseplates 12, 14, respectively. The contiguous positioning of the beveled edges 42 of the base 36 with the corresponding beveled edges 59, 93 of the slots 58, 92, respectively, prevents the guide peg 18 from tilting or rotating with respect to the inferior and superior baseplates 12, 14. The beveled edges 42 of the guide peg 18 are sized and shaped to freely slide and remain in constant contact with the corresponding beveled edges 59, 93 of the slots 58, 92 of the inferior and superior baseplates 12, 14, respectively, during expansion of the cage 10.

As shown in FIG. 3, the inferior and superior baseplates 12, 14 form a cavity 114 in the expanded conformation position of the cage 10. More particularly, the cavity 114 is bounded by the bearing surfaces 64, 98 of the inner surfaces 46, 80 of the inferior and superior baseplates 12, 14, respectively. Each of the bearing surfaces 64, 98 has a horizontal dimension which is equal to the length along the major axis A-A of the maximally sized insert 16 plus twice the height of the protuberances 30. The guide grooves 66, 100 of the inferior and superior baseplates 12, 14, respectively, channel and guide the movement of the protuberances 30 of the insert 10. More particularly, the width and depth of the guide grooves 66, 100 substantially matches the width and heights of the protuberances 30 such that the protuberances 30 are in constant contact with the guide grooves 66, 100 during its rotation. The guide grooves 66, 100 are parallel to the flat areas 56, 90 of the inferior and superior baseplates 12, 14, and extend from the corresponding bearing surfaces 64, 98 through to the mid point on inner surfaces 46, 80 of the inferior and superior baseplates 12, 14, respectively, thereby preventing the rotation of the insert 16 in excess of 90 degrees. The configuration of the cavity 114 and the guide grooves 66, 100 are such that when the insert 16 is inserted in the assembled inferior and superior baseplates 12, 14 in the non-expanded conformation position, the protuberances 30 align with the guide grooves 66, 100. The lock grooves 68, 102 are centered on the corresponding bearing surfaces 64, 98, and extend towards the distal ends 52, 86 of the inferior and superior endplates 12, 14, respectively. The lock grooves 68, 102 are sized and shaped so as to match the geometry and dimensions of the protuberances 30 of the insert 16 for purposes that are described below.

In operation, the inferior baseplate 12, the superior baseplate 14, and the guide peg 18 are preassembled in the non-expanded conformation position. The insert 16 is then initially placed between the inferior and superior baseplates 12, 14 with the minor axis B-B oriented perpendicular to the bearing surfaces 64, 98 creating the non-expanded conformation shown in FIG. 5. More particularly, the insert 16 is slid into the cavity 114 and it is centered by sliding its cavity 34 over the peg 44 of guide peg 18. The centering ensures that the insert 16 is secured on the guide peg 18 and its protuberances 30 are aligned with the guide grooves 66, 100 of the inferior and superior baseplates 12, 14.

The cage 10 is then implanted in the spine with the assistance of some impacts on the flat areas 56, 90 of the inferior and superior baseplates 12, 14 (not shown in the Figures). The appropriate hand tool (not shown in the Figures) is then inserted into the cavity 32 of the insert 16 and it is rotated 90 degrees to a position such that the major axis A-A is perpendicular to the bearing surfaces 64, 98, creating the expanded conformation position as shown in FIGS. 1-4. The rotation of the insert 16 causes the inferior and superior baseplates 12, 14 to move opposite each other, thus expanding the cage 10 to the predetermined height. More particularly, the rotation of the insert 16 from the collapsed position to the expanded position forces the inferior and superior baseplates 12, 14 to part, thus expanding the height of the cage 10, creating an optimal fit. The insert 16 is then secured in the expanded conformation position by positioning it in the lock grooves 68, 102 of the inferior and superior baseplates 12, 14, respectively. More particularly, the insert 16 is pushed inwardly (i.e., towards the distal ends 52, 86 of inferior and superior baseplates 12, 14) so as to lodge the protuberances 30 within the lock grooves 68, 102 of the inferior and superior baseplates 12, 14, thereby securing the insert 16 and preventing it from rotating and the cage 10 from collapsing. The flat surfaces 28 of the insert 16 bear squarely on the bearing surfaces 64, 98 of the inferior and superior baseplates 12, 14, thereby providing rigid support and a fixed height for the cage 10.

It should be appreciated that the present invention provides numerous advantages over the prior art discussed above. For instance, the non-expanded conformation position of the cage 10 facilitates the implantation of the cage 10 in the spine. Once implanted, the height of the cage 10 is easily increased to the expanded conformation position by simply rotating the insert 16 ninety (90) degrees. The expanded cage 10 is strong and stable and maintains its final height once expanded. Because the angle L is applied only to the superior baseplate 14, the appropriately lordosed superior baseplate 14 can be used with any insert 16, inferior baseplate 12, and/or guide peg 18, thus simplifying the adjustability of the cage 10 to create an optimal fit. The angle L remains constant throughout the expansion of the cage 10, since no hinges or other mechanisms are employed that could alter the angle L during expansion. Thus, the determination of the angle L is greatly simplified and therefore inherently more accurate since the angle L is always equal to the lordotic angle.

As a result of the foregoing, the cage 10 allows for potential significant decrease in the number of complications that arise as a result of the use of the prior art devices described above. The intraoperative adjustable height of the cage 10 will ensure an optimal fit, thus allowing for enhanced fusion. The ability to expand the cage 10 within the disc space will significantly decrease the amount of abrasion to the endplates, as no coercion will be necessary to impact the cage 10. This reduction in abrasion, in turn, will prevent any related inflammatory response, decreasing the risk of aseptic loosening. A decrease in endplate preparation would also be seen, as the endplates would not need to be precisely cut to match the height and shape of the cage 10. During expansion of the cage 10, adequate purchase into the bony endplate will be assured, as the cage 10 can be used to distract the disc space the final 0.5-1 mm, firmly anchoring it into the endplate. This secure fixation will provide a secure bone-implant interface and prevent laxity or migration. As a result, micromotions will be kept to a minimum, promoting sufficient bone ingrowth. The reduction in endplate preparation and the easier implantation method will also substantially lessen the surgical time and effort and decrease the amount of trauma to the patient. The enhanced positioning, decreased endplate preparation and abrasion, secure fixation, and reduction in surgical time achieved by the cage 10 could ultimately decrease the number of revision surgeries performed. The patient and surgeon will therefore be saved the time and stress associated with a revision, and the hospital will be saved the cost of additional surgeries.

Moreover, the cage 10 provides for a non-screw insertion, in that it allows for parallel distraction, thereby reducing the incidence of posterior nerve root compression during the distraction process. Since the cage 10 distracts in parallel, no undo stresses are placed upon the device due to permanent deformation of the device material.

It should be understood that the embodiment described herein is merely exemplary and that a person skilled in the art may make many variations and modifications without departing from the spirit and scope of the invention. For instance, the cage 10 may be coated with an osteoconductive material to provide enhanced osteointegration. Upon the application of this coating, the staircase pattern of the domes 72, 106 of the inferior and superior baseplates 12, 14, respectively, will take on a continuous dome shape. Other surface textures may be employed on the outer surfaces 48, 82 of the inferior and superior surfaces 12, 14. In the expanded conformation position of the cage 10, the cavity 114 may be packed with bone particles or bone substitute, if desired. Accordingly, all such variations and modifications are intended to be included within the scope of the invention as defined in the appended claims.

What is claimed is:
1. An intervertebral fusion cage, comprising:
an inferior baseplate having an interior surface and an exterior surface, an upper end and a lower end opposite said upper end, a lock groove formed within said interior surface, and at least one slot extending from said upper end to a point intermediate said upper and lower ends;
a superior baseplate having an interior surface and an exterior surface, an upper end and a lower end opposite said upper end of said superior baseplate, a lock groove formed within said interior surface of said superior baseplate, and at least one tab projecting from said exterior surface of said superior baseplate and extending from said upper end of said superior baseplate to said lower end of said exterior baseplate, said at least one slot of said inferior baseplate is sized and shaped to receive slidably said at least one tab of said superior baseplate when said inferior and superior baseplates are assembled with one another, said interior surfaces of said inferior and superior baseplates form a cavity when said inferior and superior baseplates are assembled with one another;
wherein said interior surface of said inferior baseplate includes a first guide groove, and said interior surface of said superior baseplate includes a second guide groove, said first and second guide grooves are sized and shaped to guide said protuberances of said insert when said insert is rotated;
a guide pin having a base and a peg projecting outwardly from said base, said base being coupled to said inferior and superior baseplates; and
an insert having a first end and a second end opposite thereof, a pair of opposed side surfaces, a pair of diametrically opposed protuberances, each of which extends outwardly from one of said pair of side surfaces, a first aperture formed within said first end, and a second aperture formed within said second end, said second aperture is sized and shaped to receive said peg of said guide pin, said guide pin enables said insert to be rotated relative thereto, each of said protuberances of said insert being releasably engageable with a corresponding one of said lock grooves of said inferior and superior baseplates when said insert is rotated relative to said guide pin, whereby when said protuberances of said insert engage said lock grooves of said inferior and superior baseplates, said inferior and superior baseplates expand from a collapsed position, in which said inferior and superior baseplates are juxtaposed with one another, and an expanded position, in which said inferior and superior baseplates are diverged away from one another, said at least one tab of said superior baseplate is continuously engaged with said at least one slot of said inferior baseplate when said inferior and superior baseplates expand from their said collapsed position to their said expanded position, whereby said inferior and superior baseplates provide for parallel distraction when they expand from their said collapsed position to their said expanded position.

2. The intervertebral fusion cage of claim 1, wherein said interior surface of said inferior baseplate includes a first bearing surface, and said interior surface of said superior baseplate includes a second bearing surface, said first and second bearing surfaces are sized and shaped to receive said insert when said insert is rotated.

3. The intervertebral fusion cage of claim 2, wherein said insert includes a width that defines a major axis, and a height that defines a minor axis, said major axis being generally parallel with said bearing surfaces of said inferior and superior baseplates they are in their said collapsed position, and said major axis being generally perpendicular to said bearing surfaces of said inferior and superior baseplates when they are in their said expanded position.

4. The intervertebral fusion cage of claim 3, wherein said insert is rotatable by approximately ninety degrees whereby said inferior and superior baseplates achieve maximum distraction when they are expanded to their said expanded position.

5. The intervertebral fusion cage of claim 4, wherein said first aperture of said insert is adapted to receive a tool for facilitating the rotation of said insert.

6. The intervertebral fusion cage of claim 1, wherein said at least one slot of said inferior baseplate includes a pair of slots, and said at least one tab of said superior baseplate includes a pair of tabs.

7. The intervertebral fusion cage of claim 1, wherein said exterior surface of said superior baseplate is angled relative to said bearing surfaces.

8. The intervertebral fusion cage of claim 1, wherein said inferior baseplate includes a first plurality of spikes disposed on said exterior surface of said inferior baseplate, and said superior baseplate includes a second plurality of spikes disposed on said exterior surface of said superior baseplate, each of said first plurality of spikes is sized and shaped to anchor said inferior baseplate to a first vertebral endplate, and each of said second plurality of spikes is sized and shaped to anchor said superior baseplate to a second vertebral endplate.

9. The intervertebral fusion cage of claim 8, wherein said inferior baseplate includes a first dome contoured to fit a concavity of the first vertebral endplate, and said superior baseplate includes a second dome contoured to fit a concavity of the second vertebral endplate.

* * * * *